United States Patent
Trejo et al.

(10) Patent No.: US 8,592,340 B2
(45) Date of Patent: Nov. 26, 2013

(54) METAL ALLOY CATALYST COMPOSITION

(75) Inventors: Jose Antonio Trejo, Lansdale, PA (US); Eric J. Langenmayr, Bryn Mawr, PA (US)

(73) Assignee: Rohm and Haas Company, Philadelphia, PA (US)

( * ) Notice: Subject to any disclaimer, the term of this patent is extended or adjusted under 35 U.S.C. 154(b) by 197 days.

(21) Appl. No.: 12/953,894

(22) Filed: Nov. 24, 2010

(65) Prior Publication Data

US 2011/0124922 A1    May 26, 2011

Related U.S. Application Data

(60) Provisional application No. 61/281,975, filed on Nov. 25, 2009.

(51) Int. Cl.
*B01J 20/22* (2006.01)

(52) U.S. Cl.
USPC .......................................... 502/401; 502/159

(58) Field of Classification Search
USPC .................................. 502/401, 159; 568/388
See application file for complete search history.

(56) References Cited

U.S. PATENT DOCUMENTS

| | | | |
|---|---|---|---|
| 4,311,811 A | 1/1982 | Manziek | |
| 4,382,124 A | 5/1983 | Meitzner et al. | |
| 6,008,416 A | 12/1999 | Lawson et al. | |
| 6,977,314 B2 | 12/2005 | Vandersall et al. | |
| 2003/0114568 A1* | 6/2003 | Sato | ................... 524/431 |
| 2005/0026772 A1 | 2/2005 | Yasunaga et al. | |
| 2008/0128649 A1 | 6/2008 | Mehrotra et al. | |

FOREIGN PATENT DOCUMENTS

| | | |
|---|---|---|
| CN | 1232015 | 10/1999 |
| CN | 101143319 | 3/2008 |
| JP | 2003200052 | 7/2003 |
| KR | 100834963 | 6/2008 |

OTHER PUBLICATIONS

Jianfeng, et al, "Preparation of Pd—Cu Bimetal Catalyst Loaded on Ion Exchange Resin . . . " Chemical Report vol. 10, pp. 765-770 (2008).

* cited by examiner

*Primary Examiner* — Colleen Dunn
*Assistant Examiner* — Haytham Soliman
(74) *Attorney, Agent, or Firm* — Carl P. Hemenway

(57) ABSTRACT

This invention relates to the composition of metal alloy-doped heterogeneous catalysts and their method of use. In particular the present invention relates to the composition and use of cost-effective metal alloy-doped ion exchange resin catalysts which provide for comparable yield and selectivity compared to the catalysts previously used.

10 Claims, No Drawings

US 8,592,340 B2

METAL ALLOY CATALYST COMPOSITION

This application claims the benefit of priority under 35 U.S.C. §119(e) of U.S. Provisional Patent Application No. 61/281,975 filed on Nov. 25, 2009.

This invention relates to the preparation of metal alloy-doped catalysts and their method of use. In particular the present invention relates to the composition and use of cost-effective metal alloy-doped ion exchange resin catalysts which provide for comparable yield and selectivity compared to the catalysts previously used.

Aldol condensation reactions involve the dimerization of a carbonyl compound (aldehyde or ketone) by the addition of the $\alpha$-carbon of one carbonyl compound to the carbonyl carbon of another to provide a $\beta$-hydroxy carbonyl compound. In the case of the condensation of two ketones in the presence of an acidic catalyst, dehydration usually occurs subsequent to dimerization to provide an $\alpha,\beta$-unsaturated ketone; reduction of the double bond using conventional techniques may be used to provide the saturated ketone adduct.

One attempt to enhance yields of methyl isobutyl ketone from the condensation reaction of acetone compared to use of conventional monosulfonated ion exchange resin catalysts is disclosed in U.S. Pat. No. 6,977,314. U.S. Pat. No. 6,977,314 discloses the use of polysulfonated ion exchange resins having at least 5.0 milliequivalents sulfonic acid groups/gram catalyst and loaded with a metal, such as palladium. The metals selected are used individually and are expensive materials. A method is needed which employs the use of metal alloy doping while maintaining catalyst lifetime, selectivity and yield and improving cost effectiveness.

The present invention solves the deficiencies of the prior art by providing a cost-effective metal alloy loaded catalyst useful to produce variety of reaction products.

The present invention provides a heterogeneous catalyst composition comprising:
(a) an ion exchange resin; and
(b) a metal alloy, based on dry weight of the catalyst;
wherein the catalyst composition reacts with reactants in a chemical reaction.

The present invention further provides a method for producing a saturated ketone adduct reactions comprising:
(a) providing a ketone reactant and
(b) contacting the ketone reacant with a catalyst composition to produce a saturated ketone adduct;
wherein the catalyst composition comprises:
(i) an ion exchange resin; and
(ii) a metal alloy, based on dry weight of the catalyst.

As used throughout the specification, the following terms shall have the following meanings, unless the context clearly indicates otherwise:

The term "crosslinked polymer matrix" refers to any crosslinked polymeric substrate that is conveniently functionalized to provide polysulfonated, monosulfonated, or partially sulfonated aromatic rings and also any crosslinked polymeric substrate that is conveniently functionalized to provide aromatic rings with amine functionality; typically the crosslinked polymer matrix is a crosslinked styrenic polymer where the aromatic rings are subjected to sulfonation conditions to provide catalysts useful in the process of the present invention.

The term "ion exchange resin" refers to a crosslinked polymer matrix having ion exchange functionality.

The term "copolymer" refers to polymer compositions containing units of two or more different monomers, including positional isomers.

The term "crosslinked copolymer" indicates a polymer or copolymer polymerized from a monomer or mixture of monomers containing at least 1 weight percent (%), based on the total monomer weight, of polyvinyl unsaturated monomer.

The term "macroporous" indicates a material that when measured by BET technique (based on the publication by Stephen Brunauer, Paul Hugh Emmett, and Edward Teller 1938) results in a surface area higher than 0.1 $m^2/g$ and lower than 2000 $m^2/g$. Typically macroporous resin catalysts of the present invention have a surface area ranging from 1 $m^2/g$ to 200 m2/g.

The term "alkyl(meth)acrylate" refers to either the corresponding acrylate or methacrylate ester; similarly, the term "(meth)acrylic" refers to either acrylic or methacrylic acid and the corresponding derivatives, such as esters or amides.

The term "doped" refers to the addition of a metallic species to a polymeric support.

The term "impregnated" refers to the metal that can be complexed or as metallic structure within the polymeric support.

The term "metal alloy" is synonymous with 'metal nanocluster' or 'metal nanoalloy'. As defined herein a metal alloy is two or more metals combined in a single nanometric size cluster. At least two of the metals in the metal alloy are present in an amount of at least 2% by weight of the total metal alloy composition. The nanometric cluster size of the metal alloy ranges from 1-250 nm. Moreover, it is a metal product containing two or more elements (1) as a solid, (2) as an intermetallic compound, or (3) as a mixture of metallic phases.

All percentages referred to will be expressed in weight percent (%), based on total weight of polymer or composition involved, unless specified otherwise. The following abbreviations are used herein: g=grams, µm=microns, cm=centimeters, mm=millimeters, m=meters, nm=nanometer, ml=milliliters, meq/g=milliequivalents/gram, L=liter, 1 bar pressure=$10^5$ Pascal or $10^5$ Pa, 1 bar=1 MPa, LHSV=Linear hourly space velocity ($h^{-1}$)=flow rate of liquid (ml/h)/volume of catalyst in column (ml), aspect ratio=length/width.

Unless otherwise specified, ranges listed are to be read as inclusive and combinable and temperatures are in degrees centigrade (° C.).

Non-limiting examples of reaction processes and their sequential combinations in one stage reaction useful in the present invention include isomerization, hydration, aldol condensation, dehydration, hydrogenolysis, nitrate reduction, oxidation, hydroformylation, selective reduction of alkenes, ketones, alcohols, alkynes and acids. Products made by the catalyzed reactions of the present invention include but are not limited to hydrogen peroxide, 1,4 butanediol, vinyl acetate, alkylphenols, methyl isobutyl ketone (MIBK), natural detergent alcohols.

The metal alloy-doped heterogeneous catalysts useful in the reaction processes of the present invention are ion exchange resins having sulfonated functionality; that is, the crosslinked polymer matrix supporting the catalyst sites contains aromatic rings having greater than 0 sulfonic acid group per aromatic ring. Typically at least 10%, alternatively at least 15%, and further alternatively at least 20% of the aromatic rings contain more than one sulfonic acid group per aromatic ring. The ion exchange resin can be either strong base anion exchange or strong acid cation exchange resins. Alternatively, the metal alloy-doped heterogeneous catalysts useful in the reaction processes of the present invention are ion exchange resins having amine functionality that is, the crosslinked polymer matrix supporting the catalyst sites contains aromatic rings having an amine group on the aromatic ring.

The metal alloy-doped heterogeneous catalysts useful in the process of the present invention may be in the form of gel or macroporous beads, films, plates, membranes, or fibers. Suitable metal alloy-doped heterogeneous catalysts of the present invention have average particle diameters from 10 μm to 1000 μm, alternatively from 500 μm to 1000 μm, and further alternatively from 750 to μm to 1000 μm; have a sulfonic acid group content of 1.0 to 7.0 meq/g, alternatively from 5.1 to 6.5 meq/g, and further alternatively from 5.2 to 6.0 meq/g, based on dry weight of ion exchange resin; typically possess a surface area from 0 to 2000, alternatively 0.1 to 2000, further alternatively from 1 to 700 and further alternatively from 10 to 600 square meters/gram ($m^2/g$); and a total porosity of 0.1 to 0.9, alternatively from 0.2 to 0.7 and further alternatively from 0.25 to 0.5 cubic centimeter pores per gram polymer ($cm^3/g$); typically possess a ratio of crosslinker in resin of from 0.5 to 80%, 5-30% 10-20% of total catalyst composition; moisture hold capacity of 80-30%, alternatively from 70-40, and further alternatively from 55-45%; a weight capacity of from 0.5-7.0 meq/Kg, alternatively from 1-6 meq/Kg, and further alternatively from 2-5 meg/Kg; with an average pore diameter of 50 to 2,500 Ångstrom units and alternatively 150 to 1000 Ångstrom units. Porosities are defined according to IUPAC (International Union of Pure and Applied Chemistry) nomenclature as follows: Microporosity=pores less than 20 Ångstrom units; Mesoporosity=pores between 20 and 500 Ångstrom units; Macroporosity=pores greater than 500 Ångstrom units The catalysts of the present invention are loaded with 0.1 to 25%, alternatively 0.5 to 15% and further alternatively 1.0 to 10.0% metal alloy, based on dry weight of ion exchange resin. Ideally, the metal-alloy may be loaded onto the shell of the ion exchange resin particle or evenly dispersed throughout the particle. With respect to the metal alloy itself, it is typically comprised of 0.5 to 100% metal, alternatively 80-100% metal and further alternatively 90-100% metal constituents. The metal alloy compositions of the present invention exist in metal cluster sizes of from 1-150 nm, alternatively from 1-50 nm, and further alternatively from 1-10 nm.

The metal alloy-doped ion exchange resins are typically prepared from crosslinked macroporous copolymers, such as those described in U.S. Pat. No. 4,382,124, in which porosity is introduced into the copolymer beads by suspension-polymerization in the presence of a porogen (also known as "phase extender" or "precipitant"), that is, a solvent for the monomer but a non-solvent for the polymer.

A typical crosslinked macroporous copolymer preparation, for example, may include preparation of a continuous aqueous phase solution containing suspension aids (such as dispersants, protective colloids and buffers) followed by mixing with a monomer mixture containing 1 to 85% polyvinylaromatic monomer, free-radical initiator and typically 0.2 to 5, alternatively 0.3 to 3 and more alternatively 0.4 to 1, parts porogen (such as toluene, xylenes, ($C_4$-$C_{10}$)-alkanols, ($C_6$-$C_{12}$)-saturated hydrocarbons or polyalkylene glycols) per one part monomer. The mixture of monomers and porogen is then polymerized at elevated temperature and the porogen is subsequently removed from the resulting polymer beads by various means; for example, toluene, xylene and ($C_4$-$C_{10}$) alcohols may be removed by distillation or solvent washing, and polyalkylene glycols by water washing. The resulting macroporous copolymer is then isolated by conventional means, such as dewatering followed by drying.

Suitable polyvinylaromatic monomers that may be used in the preparation of the crosslinked copolymers include, for example, one or more monomer selected from the group consisting of divinylbenzene, trivinylbenzene, divinyltoluene, divinylnaphthalene and divinylxylene; it is understood that any of the various positional isomers of each of the aforementioned crosslinkers is suitable; alternatively the polyvinylaromatic monomer is divinylbenzene. Typically the crosslinked copolymer comprises 1 to 85%, alternatively 5 to 55% and more alternatively 10 to 25%, polyvinylaromatic monomer units.

Optionally, non-aromatic crosslinking monomers, such as ethyleneglycol diacrylate, ethyleneglycol dimethacrylate, trimethylolpropane triacrylate, trimethylolpropane trimethacrylate, diethyleneglycol divinyl ether and trivinylcyclohexane, may also be used in addition to the polyvinylaromatic crosslinker. When used, the non-aromatic crosslinking monomers typically comprise as polymerized units, from zero to 10%, alternatively from zero to 5%, and more alternatively from zero to 2% of the macroporous polymer, based on the total monomer weight used to form the macroporous copolymer.

Suitable monounsaturated vinylaromatic monomers that may be used in the preparation of crosslinked copolymers include, for example, styrene, α-methylstyrene, ($C_1$-$C_4$) alkyl-substituted styrenes, halo-substituted styrenes (such as dibromostyrene and tribromostyrene), vinylnaphthalene and vinylanthracene; alternatively the monounsaturated vinylaromatic monomer is selected from one or more of the group consisting of styrene and ($C_1$-$C_4$)alkyl-substituted styrenes. Included among the suitable ($C_1$-$C_4$)alkyl-substituted styrenes are, for example, ethylvinylbenzenes, vinyltoluenes, diethylstyrenes, ethylmethylstyrenes and dimethylstyrenes; it is understood that any of the various positional isomers of each of the aforementioned vinylaromatic monomers is suitable.

Alternatively the copolymer comprises 15 to 99%, and alternatively 75 to 90%, monounsaturated vinylaromatic monomer units.

Optionally, non-aromatic monounsaturated vinyl monomers, such as aliphatic unsaturated monomers, for example, vinyl chloride, acrylonitrile, (meth)acrylic acids and alkyl (meth)acrylates may also be used in addition to the vinylaromatic monomer. When used, the non-aromatic monounsaturated vinyl monomers typically comprise as polymerized units, from zero to 10%, alternatively from zero to 5%, and more alternatively from zero to 2% of the macroporous copolymer, based on the total monomer weight used to form the macroporous copolymer.

Porogens useful for preparing macroporous copolymers include hydrophobic porogens, such as ($C_7$-$C_{10}$)aromatic hydrocarbons and ($C_6$-$C_{12}$)saturated hydrocarbons; and hydrophilic porogens, such as ($C_4$-$C_{10}$)alkanols and polyalkylene glycols. Suitable ($C_7$-$C_{10}$)aromatic hydrocarbons include, for example, one or more of toluene, ethylbenzene, ortho-xylene, meta-xylene and para-xylene; it is understood that any of the various positional isomers of each of the aforementioned hydrocarbons is suitable. Alternatively the aromatic hydrocarbon is toluene or xylene or a mixture of xylenes or a mixture of toluene and xylene. Suitable ($C_6$-$C_{12}$) saturated hydrocarbons include, for example, one or more of hexane, heptane and isooctane; alternatively, the saturated hydrocarbon is isooctane. Suitable ($C_4$-$C_{10}$)alkanols include, for example, one or more of isobutyl alcohol, tort-amyl alcohol, n-amyl alcohol, isoamyl alcohol, methyl isobutyl carbinol (4-methyl-2-pentanol), hexanols and octanols; alternatively, the alkanol is selected from one or more ($C_5$-$C_8$) alkanols, such as, methyl isobutyl carbinol and octanol.

Polymerization initiators useful in preparing copolymers include monomer-soluble initiators such as peroxides, hydroperoxides and related initiators; for example benzoyl peroxide, tert-butyl hydroperoxide, cumene peroxide, tetralin peroxide, acetyl peroxide, caproyl peroxide, tert-butyl peroctoate (also known as tert-butylperoxy-2-ethyl hexanoate), tort-amyl peroctoate, tert-butyl perbenzoate, tert-butyl diperphthalate, dicyclohexyl peroxydicarbonate, di(4-tert-butylcyclohexyl) peroxydicarbonate and methyl ethyl ketone peroxide. Also useful are azo initiators such as azodiisobutyronitrile, azodiisobutyramide, 2,2'-azo-bis(2,4-dimethylvaleronitrile), azo-bis(α-methylbutyronitrile) and dimethyl-, diethyl- or dibutyl azo-bis(methylvalerate). Preferred peroxide initiators are diacyl peroxides, such as benzoyl peroxide, and peroxyesters, such as tert-butyl peroctoate and tert-butyl perbenzoate; more alternatively, the initiator is benzoyl peroxide. Typical use levels of peroxide initiator are 0.3% to 5%, alternatively from 0.5 to 3% and more alternatively from 0.7 to 2%, based on the total weight of vinyl monomers.

Alternatively, the crosslinked copolymers are selected from the group consisting of divinylbenzene copolymer, styrene-divinylbenzene copolymer, divinylbenzene-ethylvinylbenzene copolymer and styrene-ethylvinylbenzene-divinylbenzene copolymer, for use as substrates for the ion exchange resin catalysts used in the process of the present invention.

These crosslinked copolymers may be functionalized with strong-acid functional groups according to conventional processes for polysulfonation known to those having ordinary skill in the art, as for example, sulfonation with sulfur trioxide ($SO_3$), fuming sulfuric acid or oleum (concentrated sulfuric acid containing sulfur trioxide) and chlorosulfonic acid; alternatively, monosulfonated cation exchange resin polymers may also be subjected to conventional polysulfonation conditions to provide a cation exchange resin catalyst.

Alternatively, these crosslinked copolymers may be functionalized with strong-, or weak base functional groups according to conventional processes known to those having ordinary skill in the art, as for example, mono-, di- or tri-alkyl amine group linked to the resin. The amine substituents could be of one, two or three whereas the structures could be:
—$CH_3$, —$(CH_2)n$-$CH_3$ (n>0 and could be from n=1 to n=8),
—$[(CH_2$—$CH_2)$—$O$—$]p$-$(CH_2$—$CH_3)$     (p>1),
—$CH_2CH_2OH$, N-methylglucamine, diethylenamine, triethylenamine functional groups.

The metal alloy-doped ion exchange resin catalysts are typically loaded with the desired metal-alloy in one of two ways: a) by forming nanoalloys within the ion exchange polymer by mixing two or more metals to form the alloy within the ion exchange polymer structure, or b) by using an ion exchange polymer metal oxide nanometric composite material and supporting the metal-alloy catalytic metals on the support surface followed by reduction. Selection of metals in forming the alloy is an important consideration.

Typically, the metal alloy-doped ion exchange resin catalysts are loaded by contacting a solution with a combination of two or more of the following: a metal salt or a metal complex with the ion exchange resin in a batch or column mode. By way of example the catalyst may be comprised of two metal salts or one metal salt and a metal complex or two metal complexes. Additionally, the metal-alloy may be provided in the form a metal-alloy salt. In this case, the loaded cation exchange resin is then rinsed free of residual salts or acid. The amount of metal-alloy salt used is chosen such that the metal or metal ion will ultimately be present in an amount ranging from 0.1 to 20% loading, alternatively about 0.5 to 10% loading and more alternatively about 1.0 to 5.0% loading of ion exchange resin, and can be determined by conventional analytical test methods.

Metal ions suitable for use as part of catalysts useful in the process of the present invention include, for example palladium (Pd), platinum (Pt), rhodium (Rh), iridium (Ir), ruthenium (Ru), copper (Cu), nickel (Ni), zinc (Zn), aluminum (Al), Gold (Au), titanium (Ti), vanadium (V), chromium (Cr), manganese (Mn), iron (Fe), cobalt (Co), silicon (Si), silver (Ag), lead (Pb), tin (Sn), niobium (Nb), molybdenum (Mo), mercury (Hg), antimony (Sb), tungsten (W), hafnium (Hf), cadmium (Cd), tin (Sn), zirconium (Zr), osmium (Os) and arsenic (As). It is contemplated by the present invention that two or more individual metals or metal complexes may be used in the alloy composition. For example, alloys may be bi-metallic or tri-metallic. Additionally, more than 3 individual metals or complexes of multiple metals may be used in the alloy compositions. Suitable examples of metal alloys of the present invention include but are not limited to Ni—Pt, Pd—Pt, Ni—Cu, Ni—Ag, Ni—Au, Cu—Pd, Cu—Pt, Pd—Ag, Pd—Au, Pt—Au, Pt—Au, Fe—Co, Fe—Ni, Co—Ni, Fe—Ag, Fe—Ag, Co—Ag, Co—Pd, Co—Rh, Co—Pd, Co—Rh, Ni—Rh, Cu—Ru, Fe—Pt, Co—Pt, Fe—Au, Co—Au, W—Au, Ni—Al, Cu—Zn, Ni—Zn, Ni—Pd, Ni—Pt, Pd—Pt, Ni—Au, Cu—Pd, Cu—Pt, Pd—Au, Pt—Au, Co—Ni, Co—Pt, Ru—Pd, Ru—Pt, Rh—Pt, Re—Ir, Mo—Pt, Fe—Zn and Cu—Zn. Particularly useful combinations of the present invention include but are not limited to Pd—Au, Pd—Ag, Fe—Co, Fe—Ni, Fe—Zn, Ni—Cu, Ni—Al, Cu—Zn, Ni—Zn, and Fe—Cu.

The ion exchange resin may be loaded with metal-alloy by a variety of methods. One example is when, for example, a cation exchange resin is loaded with metal alloy by passing an aqueous solution of the metal-alloy salt through a column of the cation exchange resin until a desired level of metal-alloy has been retained by the resin—this is followed by thorough washing with water to remove residual salts and acid generated during the loading process.

In another embodiment, the catalyst of the present invention is manufactured using a borone reducing resin. Examples of such resin are disclosed in U.S. Pat. No. 4,311,811. Such resins are put in contact with a solution containing two or more metals which can be reduced. When contacting the solution with the resin the metal salts enter the resin structure and are reduced to zero valent metal alloys. The metal loading in the resin can be from 0.01%-w dry basis to 55%-w-dry basis of the resin alternatively from 5 to 25 and further alternatively from 8 to 15.

Alternatively, the catalyst is prepared by reducing an ion exchange resin containing metal ions to deposit the metal-alloy in the catalyst. In this case the metal loaded resin may be subjected to 'activation' (reduction to zero valent state of the metals) by exposing the metal loaded resin to hydrogen (typically at room temperature with hydrazine and low partial pressures of hydrogen, for example, less than 1 bar). Typical reduction reactions use, for example, hydrogen, sodium borohydrate, hydrazine, ethylenglycol as the reductant in the reaction. The resin can then be thermally treated.

Alternatively, the activation may be conducted at room temperature 40° C. to 200° C., preferably from 60° C. to 150° C. and most preferably from 80-100-° C. and/or at hydrogen pressures of about 2 to 50 bar. The loaded catalyst containing the metal-alloy in reduced form may then be used as desired in the catalyzed reactions such as for example condensation reactions. Alternatively, the loaded resin (metal in ionic form) may be 'activated' to the reduced metal form just prior to use in a condensation reaction. When Pd, Pt, Rh, Ir, or Ru are used in the metal-alloy component of the catalyst for example, the loaded resin may be activated to the reduced metal form prior to being used in the condensation reaction. In some instances the resin loaded catalyst may be carbonized. By carbonized, it is meant that the catalyst is pyrolized under reducing conditions and is heated to a temperature from 600-1000° C. resulting in a carbonaceous bead structure.

Ideally during the reaction processes a reaction temperature is maintained from, 50° C. to 800° C., alternatively from 75 to 600° C., and further alternatively from 75 to 175° C. Pressure is maintained at from 1 to 150 bar, alternatively from 20-100 bar, and further alternatively from 30-80 bar. LHSV (liquid hourly space velocity) ranges from 0.1 to 20 h−1, alternatively from 2 to 20 h−1, further alternatively from 5 to 20 h−1. The reactor configurations within the reaction system may be any of those known to the ordinarily skilled in the art. Such configurations include but are not limited to packed column, mixed reactor, continuous stirred reactor (CSTR), loop reactor, and moving bead reactors. Additionally, there may be flow through in the system of gas, liquid or combinations of the two. The reaction may be conducted batch-wise or continuously.

By way of a non-limiting example, in one embodiment, a metal-alloy doped sulfonated resin catalyst is in the physical form of beads contained in a vessel, the beads forming a bed of the catalyst. A feed stream of ketone reactant, such as acetone, is brought into contact with the catalyst bed in the presence of hydrogen (as a separate feed stream) for a sufficient time and temperature for the condensation reaction of the ketone to occur. The condensed liquid stream, containing reaction products (saturated ketone adduct), byproducts (unsaturated ketone adduct) and any unreacted ketone reactant which may be present, is separated from the catalyst bed, and desired ketone adduct is recovered from the liquid stream by conventional separations means (such as distillation). One of ordinary skill in the art will be able to choose appropriate conditions, such as (1) batch operation, for example, in which the catalyst bed is loaded with the liquid stream in the presence of hydrogen, followed by removal of the liquid stream from the catalyst after the desired reaction has occurred, or (2) the more preferred continuous operation, for example, where the liquid stream is fed continuously into one end of a column reactor (with hydrogen) at a rate that allows sufficient residence time in the catalyst bed for the desired reaction to occur, with the condensed liquid stream being removed continuously from the other end of the bed. Similarly, the reaction equipment, the choice of upflow or downflow for the direction of passage of the reactant streams through the bed, the reaction time and temperature, the particular reactants, and the method of recovering the ketone adduct, are readily selected based upon the guidance provided herein and the knowledge available to one of ordinary skill in the art.

Typically, the temperatures and pressures inside the column reactor are selected so that the ketone reactant is at its boiling point in the catalyst bed. Variation of temperature/pressure of the ketone reactant is used to provide the desired combination of reaction temperature and conditions such that the condensation reaction takes place in the liquid phase in the catalyst bed. Conditions may be varied to provide gas phase conditions with the catalyst bed; however, it is preferred that the conditions are such that the condensation reaction is conducted in the liquid phase.

The metal-alloy doped sulfonated resin catalysts of the present invention may be used in condensation reactions where the ketone reactant and hydrogen are contacted under batch reaction conditions or under continuous reaction conditions. In one embodiment of the invention the process is a continuous process based on a catalytic distillation process with the introduction of the ketone reactant being into the bottom of a column reactor immediately above a reboiler stage; in this case the product fraction or stream is withdrawn continuously from the reboiler portion of the distillation apparatus for further processing (see U.S. Pat. No. 6,008,416 for further general and specific details of catalytic distillation processes). Alternatively, the ketone reactant to undergo the condensation reaction is fed downward through the catalyst bed and a current of hydrogen is passed through the reaction zone in the same direction. However, other variations of introducing the reactant feed streams may be used, such as co-current and countercurrent hydrogen flow, flooding processes and gaseous-phase processes.

For continuous processes, the amount of catalyst to be used, relative to the amount of reactants, is typically related to the throughput rate of the reactions, as indicated by the LHSV (liquid hourly space velocity) or liquid flow rate of reactants relative to the volume of catalyst per unit time. Typically, high LHSV are desirable to maximize equipment usage and generation of product; however meeting this objective must be balanced against % conversion of raw materials and % selectivity to the desired product. If the LHSV is too low, production rate of the desired product (space-yield) is diminished and the process may not be economical. If the LHSV is too high, the catalyst activity will be insufficient to provide the desired level of conversion (the process becomes "kinetically limited"). Suitable values of LHSV will typically range from 0.5 and $10^{-1}$, alternatively from 1 to 8 h$^{-1}$ and more alternatively from 2.5 to 6 h$^{-1}$.

Typically, the ketone reactant is contacted with hydrogen in presence of the catalyst at a temperature of 110 to 170° C. and at a pressure from 1 to 100 bar of hydrogen. Suitable temperatures for conducting the catalyzed condensation reactions of the present invention are from 110 to 170° C., alternatively from 120 to 160° C. and more alternatively from 130 to 150° C. In general, the reaction zone of the ketone reactant and hydrogen is maintained at a pressure of 1 to 100 bar of hydrogen, alternatively from 5 to 60 bar and more alternatively from 10 to 40 bar. Typically, the condensation reaction is conducted at a hydrogen/ketone reactant molar ratio of 0.1 to 1 and alternatively from 0.15 to 0.5.

In another embodiment of the invention, the process may be a batch one with the introduction of the ketone reactant into a reactor column at the reboiler section stage of a catalytic distillation apparatus (similar to that described above). The process may then be terminated when a desired product composition of ketone adduct is achieved in the reboiler section. Alternatively, the condensation may be carried out in a batch autoclave reactor for a specified period of time, followed by cooling and recovery of the desired of the ketone adduct by distillation or other conventional means.

EXAMPLE 1

Pd—Au Strong Acid Cationic Resin Catalyst

This example describes the synthesis of Pd—Au metallic alloy in an acid strong acid polymeric bead. The metal loading in %-weight dry basis of the catalyst is 0.5%-w of metal. The strong acid cationic resin was dried. 10 g of dried polymer were mixed with 10 g of aqueous solution containing $HAuCl_4*3H_2O$ salt (50%-w of Au). 0.3 g Au was mixed to the resin and equilibrated for 3 minutes with agitation. The incipient wetness method delivered an Au impregnated catalyst. The catalyst was dried and mixed with aqueous solution containing Pd solution to impregnate 0.1 g Pd to the catalyst.

The catalyst was reduced with Hydrogen at 100° C. for 24 hours under Hydrogen pressure of 300 psi.

COMPARATIVE EXAMPLE 2

Pd Strong Acid Cationic Resin Catalyst

A commercial Pd loaded resin was used for this example: This example describes the synthesis of Pd in an acid strong acid polymeric bead. The metal loading in %-weight dry basis of the catalyst is 0.5%-w of metal. The strong acid cationic resin was dried. 10 g of dried polymer were mixed with 10 g of aqueous solution containing Pd salt. An incipient wetness method delivered a Pd impregnated catalyst. The catalyst was reduced with Hydrogen at 100° C. for 24 hours under Hydrogen pressure of 300 psi. The metal cluster size was measured by TEM and XRD to be within 1-15 nm.

EXAMPLE 3

MIBK Testing Example

A flow through reaction was used to test the catalysts from example 1 and 2. Acetone was flowed at 1.6 LHSV (h−1), Hydrogen flow rate of 170 ml/min, Pressure at 400 psi and Temperature of 135° C. The conversion, yield and selectivity was measured by GC (gas chromatography) after 8 hours with a carbon-carbon accountability of 99%.

|  | Conversion (%) | MIBK Selectivity (%) |
|---|---|---|
| Example 1: Au—Pd | 49 | 94 |
| Comparative Example 2: Pd | 44 | 90 |

The invention claimed is:

1. A catalyst composition comprising:
   (a) a sulfonated ion exchange resin; and
   (b) a metal alloy, present in an amount ranging from 0.1 to 20 wt. %,
      wherein the metal alloy comprises at least two of the metals selected from the following:
      palladium (Pd), platinum (Pt), rhodium (Rh), iridium (It), ruthenium (Ru), copper (Cu), nickel (Ni), zinc (Zn), aluminum (Al), gold (Au), titanium (Ti), vanadium (V), chromium (Cr), manganese (Mn), iron (Fe), cobalt (Co), silicon (Si), silver (Ag), lead (Pb), tin (Sn), niobium (Nb), molybdenum (Mo), mercury (Hg), antimony (Sb), tungsten (W), hafnium (I-If), cadmium (Cd), tin (Sn), zirconium (Zr), osmium (Os) and arsenic (As),
   and wherein the catalyst is, made by a process comprising:
      (i) loading the resin by contacting the resin with a solution containing two or more moieties selected from salts, complexes, and mixtures thereof of said metals, and
      (ii) then reducing the metals to zero valent state by exposing the loaded resin to hydrogen, sodium borohydrate, hydrazine, or ethylene glycol;
   wherein the process deposits the metal alloy in the catalyst.

2. The catalyst composition of claim 1 wherein at least 1 of the at least two metals is a complex of multiple metals.

3. The catalyst composition of claim 1 wherein the catalyst comprises 0.01 to 25 percent metal-alloy based on dry weight of the catalyst.

4. The catalyst composition of claim 1 wherein the metal alloy comprises a metal cluster size of from 1-250 nm.

5. The catalyst composition of claim 1 wherein the catalyst is in the form of macroporous beads having a total porosity of 0.1 to 0.9 cubic centimeters per gram and a surface area of 10 to 100 square meters per gram, based on dry weight of the catalyst.

6. The catalyst composition of claim 1 wherein the catalyst is in the form of gel beads.

7. The catalyst composition of claim 1 wherein the catalyst is pyrolized.

8. The catalyst composition of claim 1, wherein the metal alloy comprises at least two of the metals selected from the following:
   palladium (Pd), platinum (Pt), rhodium (Rh), iridium (Ir), nickel (Ni), zinc (Zn), iron (Fe), and tungsten (W).

9. The catalyst composition of claim 5, wherein said macroporous beads comprise a crosslinked copolymer, which comprises 1 to 85% polyvinylaromatic monomer units.

10. The catalyst composition of claim 1,
   wherein said ion exchange resin is crosslinked macroporous copolymer beads, and
   wherein said catalyst is prepared by a process comprising contacting said ion exchange resin with a solution of two or more of a metal salt or a metal complex.

* * * * *